United States Patent
Tominaga et al.

(10) Patent No.: US 6,707,549 B2
(45) Date of Patent: Mar. 16, 2004

(54) MOLECULAR SENSOR AND RAMAN SPECTROSCOPY PROCESS

(75) Inventors: Junji Tominaga, c/o Tsukuba Central 4, National Institute of Advanced Industrial Science and Technology of 1-1, Higashi 1-chome Tsukuba-shi, Ibaraki 305-8562 (JP); Masashi Kuwahara, c/o Tsukuba Central 4, National Institute of Advanced Industrial Science and Technology of 1-1, Higashi 1-chome, Tsukuba 305-8562 (JP); Christophe Mihalcea, Tsukuba (JP); Dorothea Buechel, IbarakiTsukuba (JP); Takashi Kikukawa, Tokyo (JP); Hiroshi Fuji, Souraku-gun (JP)

(73) Assignees: TDK Corporation, Tokyo (JP); National Institute of Advanced Industrial Science and Technology, Tokyo (JP); Junji Tominaga, Tsukuba (JP); Masashi Kuwahara, Tsukuba (JP)

( * ) Notice: Subject to any disclaimer, the term of this patent is extended or adjusted under 35 U.S.C. 154(b) by 12 days.

(21) Appl. No.: 10/095,938

(22) Filed: Mar. 13, 2002

(65) Prior Publication Data

US 2002/0145735 A1 Oct. 10, 2002

(30) Foreign Application Priority Data

Mar. 14, 2001 (JP) .......................... 2001-073181

(51) Int. Cl.$^7$ ............................. G01J 3/44; G01N 21/65
(52) U.S. Cl. ....................................................... 356/301
(58) Field of Search ......................................... 356/301

(56) References Cited

FOREIGN PATENT DOCUMENTS

| JP | 2000-356587 | 12/2000 | |
|---|---|---|---|
| WO | WO 98/09153 | * 3/1998 | ................. 356/301 |

OTHER PUBLICATIONS

A. Brioude et al., "Raman Spectroscopy of Sol–Gel Ultrathin Films Enhanced by Surface Plasmon Polaritons". Journal of Applied Physics, vol. 68, No. 11. Dec. 1, 2000, pp. 6187–6191.

* cited by examiner

Primary Examiner—F. L. Evans
(74) Attorney, Agent, or Firm—Oblon, Spivak, McClelland, Maier & Neustadt, P.C.

(57) ABSTRACT

A molecular sensor comprising a sensor film containing a metal compound wherein Raman spectroscopic analysis is carried out utilizing the amplification of Raman light by the localized plasmons that fine particles resulting from reduction of the metal compound generate has a small size and a very high sensitivity. A high sensitivity Raman spectroscopic process is provided.

21 Claims, 4 Drawing Sheets

MOLECULAR SENSOR AND RAMAN SPECTROSCOPY PROCESS

This invention relates to a molecular sensor for sensing molecules by Raman spectroscopy and a Raman spectroscopic process.

BACKGROUND OF THE INVENTION

It is known that Raman light can be amplified by the plasmons generated on the surface of a metal thin film.

For example, J. Appl. Phys., Vol. 88, No. 11, pp. 6187–6191, Dec. 1, 2000, describes Raman spectroscopy of thin films enhanced by surface plasmon polaritons. In this article, utilizing the surface plasmon resonance of a silver thin film formed on a glass substrate, Raman spectroscopy is carried out on a $TiO_2$ thin film on the Ag thin film.

In FIG. 4 of the article, Configurations A, B and C are illustrated as the optical setup for Raman spectroscopy. In Configuration A, a prism is located beneath the glass substrate, laser light is incident on the Ag thin film from the prism for total reflection at the lower surface of the Ag thin film, and Raman light is detected at the top of the $TiO_2$ thin film. Configuration B is identical with Configuration A in that the prism is located beneath the glass substrate, but laser light is incident on the Ag thin film from above the $TiO_2$ thin film. Configuration C is identical with Configuration B in that laser light is incident on the Ag thin film from above the $TiO_2$ thin film, but the prism is removed. Of the three optical setups, Configuration A affords the highest intensity of Raman light. No Raman spectrum is detected from Configuration C without the prism.

It is understood from the above article that a total reflection prism must be used in order to amplify Raman light by surface plasmon resonance. However, the provision of a total reflection prism requires to increase the size of device. Also, the necessity to set a fixed incident angle of laser light decreases the freedom of design of the device configuration.

On the other hand, JP-A 2000-356587 describes a localized plasmon resonance sensor. This sensor includes a substrate and metal fine particulates secured to the substrate surface in film form and having a diameter of 10 to 20 nm. The advantage alleged therein is that utilizing the localized plasmons generated in proximity to surfaces of metal fine particulates, the sensor dispenses with a total reflection prism. The metal fine particulates secured to the substrate surface in film form are formed by immersing a glass substrate in a 10% methanol solution of 3-aminopropyltrimethoxysilane for 10 minutes, washing the substrate and immersing it in a gold colloidal solution for 2 hours.

The sensor of the above-referred JP-A 2000-356587 is an affinity sensor which measures the absorbance of light transmitted by metal fine particulates for thereby detecting the refractive index of a medium in proximity to the metal fine particulates, and thereby determines whether any substance is adsorbed to the metal fine particulates. It is not a Raman spectroscopic sensor capable of determining the species of molecules.

A study of the present inventors has revealed that a practical level of sensitivity is not reached when Raman spectroscopy is carried out using the sensor of the above-referred JP-A 2000-356587. This is presumably because in the gold fine particulate monolayer film formed by binding gold colloid to the glass substrate surface, the distance between gold fine particulates arrayed is too large, which results in generation of less localized plasmons and hence, insufficient amplification of Raman light. In addition, the gold fine particulate monolayer film formed by binding gold colloid, the distance between gold fine particulates arrayed is relatively large and the uniformity of array density is relatively low as seen from FIG. 5 (SEM photomicrograph) of the patent publication. This also accounts for insufficient amplification of Raman light.

SUMMARY OF THE INVENTION

An object of the present invention is to reduce the size and increase the sensitivity of a molecular sensor which carries out Raman spectroscopy utilizing the amplification of Raman light by plasmons, and to provide a high sensitivity Raman spectroscopic process.

In a first aspect, the invention provides a molecular sensor comprising a sensor film containing a metal compound wherein Raman spectroscopic analysis is carried out utilizing the amplification of Raman light by the localized plasmons that fine particles resulting from reduction of said metal compound generate.

In a preferred embodiment, the sensor film has been formed by physical vapor deposition. Preferably, the metal compound is reduced by irradiating electromagnetic wave or with exciting light used in the Raman spectroscopic analysis. The metal compound is preferably a metal oxide or metal halide and typically contains Ag.

In a second aspect, the invention provides a Raman spectroscopic process utilizing the amplification of Raman light by the localized plasmons that fine particles consisting essentially of a metal generate. Preferably the fine particles are formed by reduction of a metal compound.

DESCRIPTION OF THE PREFERRED EMBODIMENTS

Figure 1:
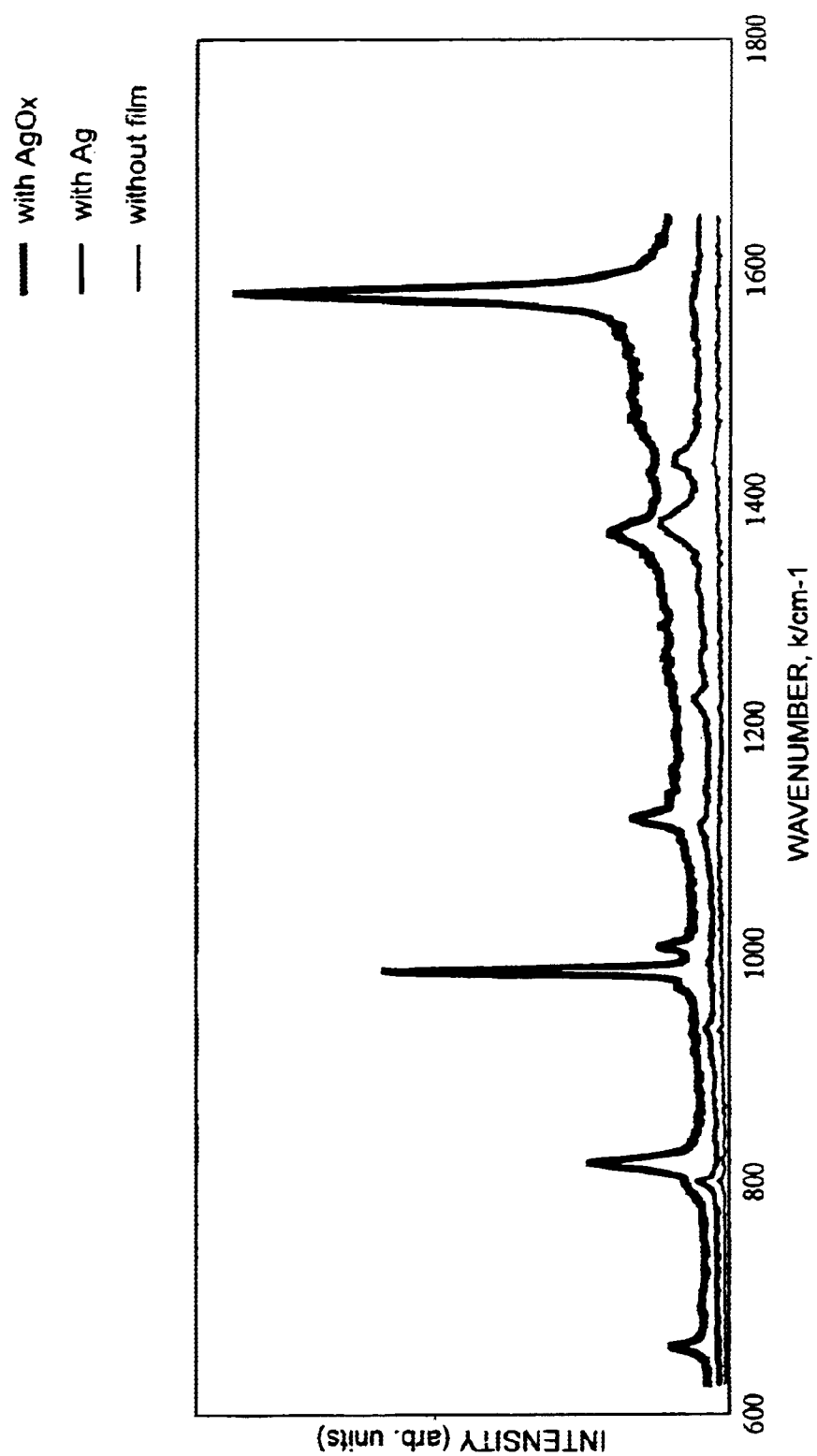
FIG. 1 is a graph showing Raman spectra of inventive and comparative sensors in Example 1.

According to the invention, in a sensor film containing a metal compound, the metal compound is chemically reduced to create fine particles, in proximity to surfaces of which localized plasmons generate. Utilizing the amplification of Raman light by the localized plasmons, Raman spectroscopic analysis is carried out.

The sensor film used herein is not critical as long as it is made of a compound which creates fine particles consisting essentially of a metal when reduced. A thin film consisting essentially of a metal oxide or metal halide is preferred.

The metal of the metal compound is one capable of generating localized plasmons, and may be selected, for example, from Ag, Au, Cu, Ti and W. A choice is preferably made of those metals which generate more localized plasmons, for example, Ag, Au and Cu, with Ag being most preferred.

The metal compound in the sensor film may have a stoichiometric composition or deviate therefrom. The composition of metal compound may be empirically determined appropriate for a particular metal species so as to increase the amplification factor of Raman light. In the case of silver oxide, for example, a composition centering at $Ag_2O$ is preferred, and illustratively, $AgO_x$ wherein x is in the range of 0.2 to 0.95, and especially 0.3 to 0.7 is preferred.

The sensor film is preferably formed by physical vapor deposition. The preferred physical vapor deposition methods are sputtering and vacuum evaporation methods, with the sputtering method being especially preferred. The sputtering method may use a metal compound as the target. Alternatively, reactive sputtering may be carried out using a metal target in a reactive gas such as oxygen. The reactive sputtering method is easy to control the composition of the sensor film by regulating the flow rate of the reactive gas. When silver oxide is used as the metal compound, for example, the flow rates of plasma gas (typically Ar) and reactive gas (typically $O_2$) during reactive sputtering are preferably set so as to give a $O_2/(Ar+O_2)$ flow ratio of from 0.1 to 0.8, especially from 0.2 to 0.5.

The substrate on which the sensor film is formed is not critical and may be either a relatively rigid substrate made, for example, of glass, resins, semiconductors or ceramics, or a flexible resin film. The use of a long web of resin film as the substrate allows the sensor film to be continuously formed on a large area substrate. If a long web of substrate having a sensor film formed thereon is used in a roll form, a necessary length of substrate section may be cut therefrom and used whenever Raman spectroscopy is carried out. The substrate surface need not be smooth, and for example, the substrate surface may be formed with a plurality of wells for receiving droplets to be analyzed.

Preferably the sensor film has a thickness of 1 to 500 nm, and more preferably 3 to 100 nm. As the sensor film is thinner, fine particles of a smaller diameter are created in the sensor film, by which the amplification factor of Raman light is enhanced. It is noted that if the sensor film is too thin, then the diameter of fine particles becomes too small, which rather reduces the amplification factor.

According to the invention, the metal compound in the sensor film is chemically reduced to create fine particles consisting essentially of the metal before Raman spectroscopy is carried out. The reduction of the metal compound often resorts to the irradiation of electromagnetic wave. The wavelength of electromagnetic wave used is not critical and may be determined as appropriate in accordance with the metal compound to be reduced. For example, when electromagnetic radiation is irradiated to a sensor film of silver oxide to cause fine silver particles to precipitate, use may be made of electromagnetic radiation having a wavelength varying from the ultraviolet to the infrared region. It may be either monochromatic light or continuous spectrum light. In another embodiment, fine particles can be precipitated during formation of the sensor film, by controlling the sputtering conditions under which the sensor film is formed, for example, by forming the sensor film while heating the substrate. In a further embodiment, fine particles can be precipitated by heat treating the sensor film under appropriate conditions after its formation.

In a still further embodiment of the invention, electromagnetic wave may be irradiated to the entire sensor film prior to Raman spectroscopy, whereupon the metal compound is reduced with exciting light used in the Raman spectroscopy. Understandably, laser light used as the exciting light causes local heating of the sensor film in which the heat then generated diffuses in in-plane directions thereof rather than transferring to the substrate. As a consequence, the metal compound can be reduced without causing deformation or decomposition of a less heat resistant resin substrate. The utilization of exciting light eliminates a need for reduction treatment of the metal compound independent of the sensing operation.

The intensity and irradiating time of electromagnetic wave may be appropriately determined so that fine particles of optimum diameter are created, depending on various other conditions including the type of metal compound and the thickness of sensor film. For example, by controlling the intensity and irradiating time of radiation with the sensor film thickness kept unchanged, the diameter of fine particles created can be adjusted. More particularly, as the intensity of radiation is higher and as the irradiating time is longer, the diameter of fine particles generally becomes larger.

The fine particles created by reduction treatment consist essentially of the metal. The presence of a metal compound component which has not been reduced is allowable as long as it does not adversely affect the amplification of Raman light. Preferably the fine particles have a mean particle size of 0.1 to 50 nm, more preferably 0.3 to 20 nm. Fine particles with too small or too large a mean particle size may lead to a lower amplification factor of Raman light. The average distance between fine particles is preferably 0.5 to 50 nm, more preferably 1 to 10 nm. Fine particles spaced too short or too long a distance may lead to a lower amplification factor of Raman light. The mean particle size of and the average distance between fine particles can be measured, for example, by means of a scanning electron microscope (SEM). The mean particle size and distance of fine particles can be controlled, for example, in terms of the composition, forming conditions and thickness of the sensor film as well as reducing conditions of the metal compound.

Now Raman spectroscopy is carried out with the molecular sensor of the invention. First, molecules to be analyzed are adsorbed on the sensor film surface or placed in proximity to the sensor film surface. A specimen containing molecules to be analyzed may be either a liquid or a gas. Then, laser light serving as the exciting light is incident on the sensor film. The interaction of exciting light with the fine particles created by irradiation of exciting light or the fine particles previously created in the sensor film enhances the electric field, by which localized plasmons are excited. The localized plasmons resonate with the vibration mode of —CN, —CH or other bonds present in the molecules to be analyzed whereby Raman light corresponding to that vibration mode is amplified. It is noted that the present invention may also utilize the resonant Raman effect.

The sensor of the invention has so high a sensitivity that detection is possible even when the concentration of molecules to be analyzed is very low, for example, the concentration of molecules in a test solution is as low as about $10^{-9}$ mol/liter.

The structure of the sensor according to the invention is not critical. For example, the structure may include, in addition to the substrate on which the sensor film is formed, a light source element for exciting light and a detection element for Raman light. The exciting light may reach the sensor film directly or through the substrate. Also, the Raman light may be detected either on the exciting light incident side or on the side of the sensor film remote from the exciting light incident side.

It is understood that in a plasmon enhanced sensor of the type using a sensor film including a total reflection prism and a metal thin film as described in the above-referred J. Appl. Phys., 88 (11), 6187–6191, Dec. 1, 2000, the sensor film according the present invention may be used instead of the metal thin film. Raman spectroscopy with a very high sensitivity is achievable in that application as well.

EXAMPLE

Examples of the invention are given below by way of illustration and not by way of limitation.

Example 1

On slide glass as the substrate, a sensor film of silver oxide whose composition was close to $Ag_2O$ was formed by a reactive sputtering method using oxygen as the reactive gas and Ag as the target. The sensor film was 15 nm thick. The flow ratio $O_2/(Ar+O_2)$ was set at 0.25 during the reactive sputtering. This is an inventive sample.

For comparison purposes, a comparative sample was prepared by baking the inventive sample at 200° C. for one hour. The sensor film of this comparative sample was an Ag film of homogeneous structure in which precipitation of fine particles was not observed.

Still for comparison purposes, another comparative sample was prepared which consisted solely of the substrate without the sensor film.

With these samples kept immersed in a test solution, laser light having a wavelength of 488 nm was irradiated to the samples, from which Raman spectra were measured. The test solution was a solution of benzoic acid in isopropanol in a concentration of $3.0 \times 10^{-3}$ mol/liter.

FIG. 1 shows the Raman spectra of these samples. It is seen from FIG. 1 that the inventive sample produces Raman light at a very high intensity as compared with the comparative sample using the homogeneous silver film as the sensor film, The present invention increases the sensitivity by a factor of about several hundred to about one thousand over the comparative sample.

After the Raman spectroscopic analysis, the sensor film of the inventive sample was observed under SEM, finding that fine Ag particles uniformly precipitated at the laser light irradiated sites. The fine Ag particles had a diameter in the range of 5 to 10 nm and a mean particle size of 7 nm. The average distance between fine Ag particles was 10 nm.

Example 2

Inventive samples were prepared as in Example 1 except that the thickness of the sensor film was set at 15 nm, 50 nm or 500 nm. As in Example 1, Raman spectroscopic analysis was carried out with these samples. The Raman spectra obtained are shown in FIG. 2.

Figure 2:
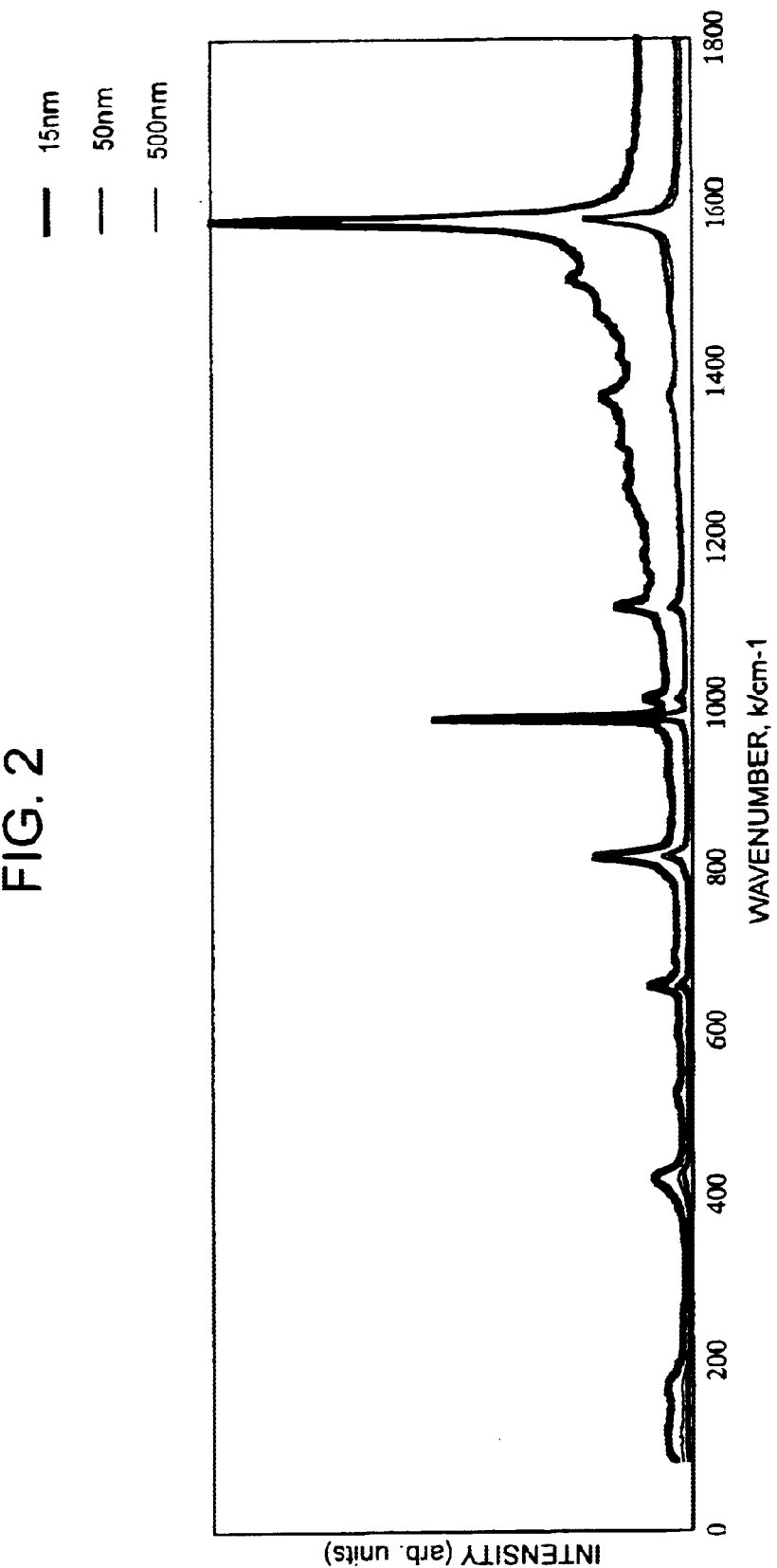
FIG. 2 is a graph showing Raman spectra of inventive sensors having different sensor film thickness.

It is evident from FIG. 2 that the amplification factor of Raman light can be controlled by regulating the thickness of the sensor film.

Example 3

Inventive samples were prepared as in Example 1 except that the flow ratio $O_2/(Ar+O_2)$ during the reactive sputtering was set at 0.25, 0.50 or 0.75. As in Example 1, Raman spectroscopic analysis was carried out with these samples. The Raman spectra obtained are shown in FIG. 3.

Figure 3:
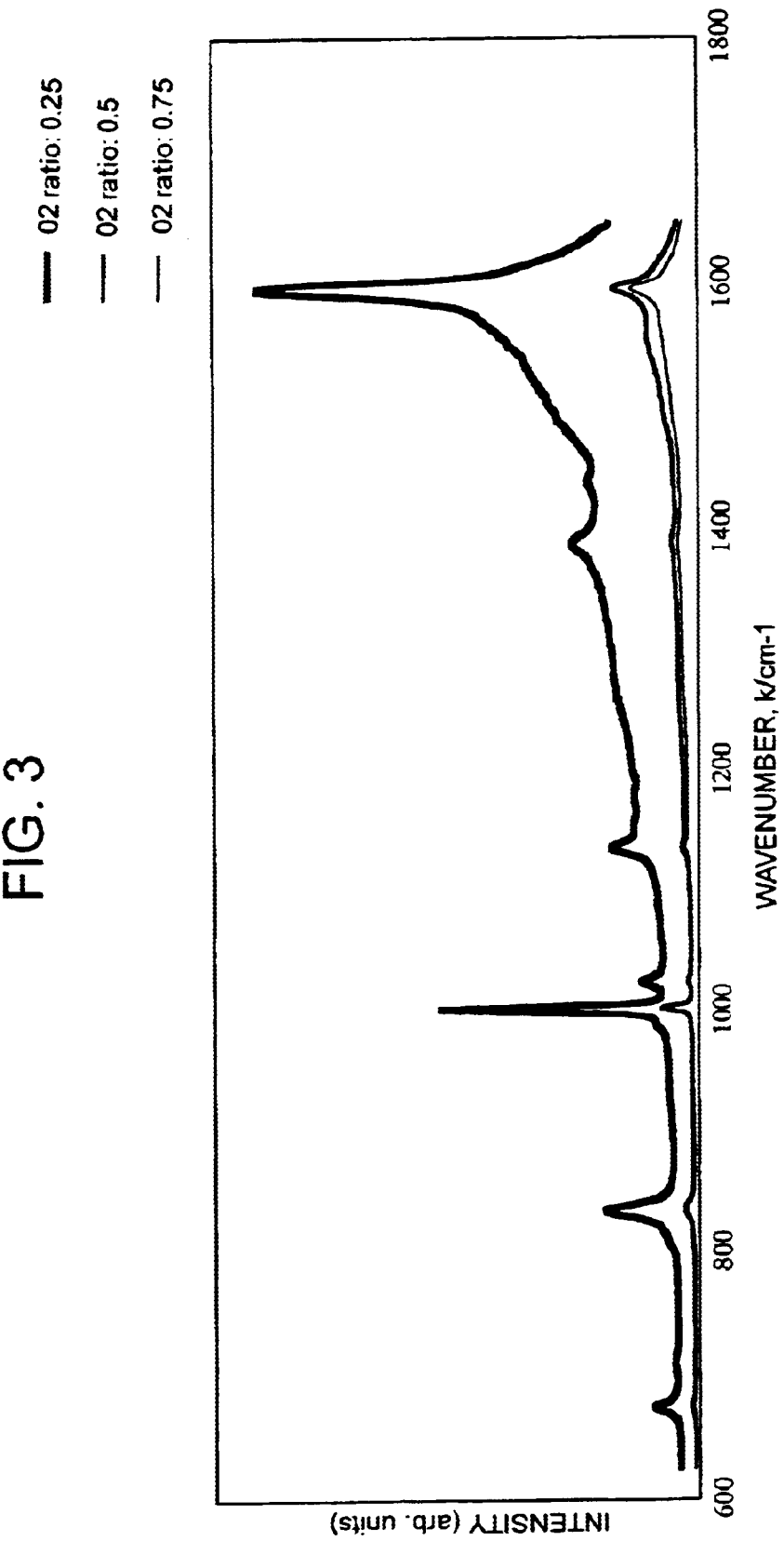
FIG. 3 is a graph showing Raman spectra of inventive sensors having different sensor film composition.

It is evident from FIG. 3 that the amplification factor of Raman light can be controlled by regulating the composition of the sensor film.

Example 4

Figure 4:
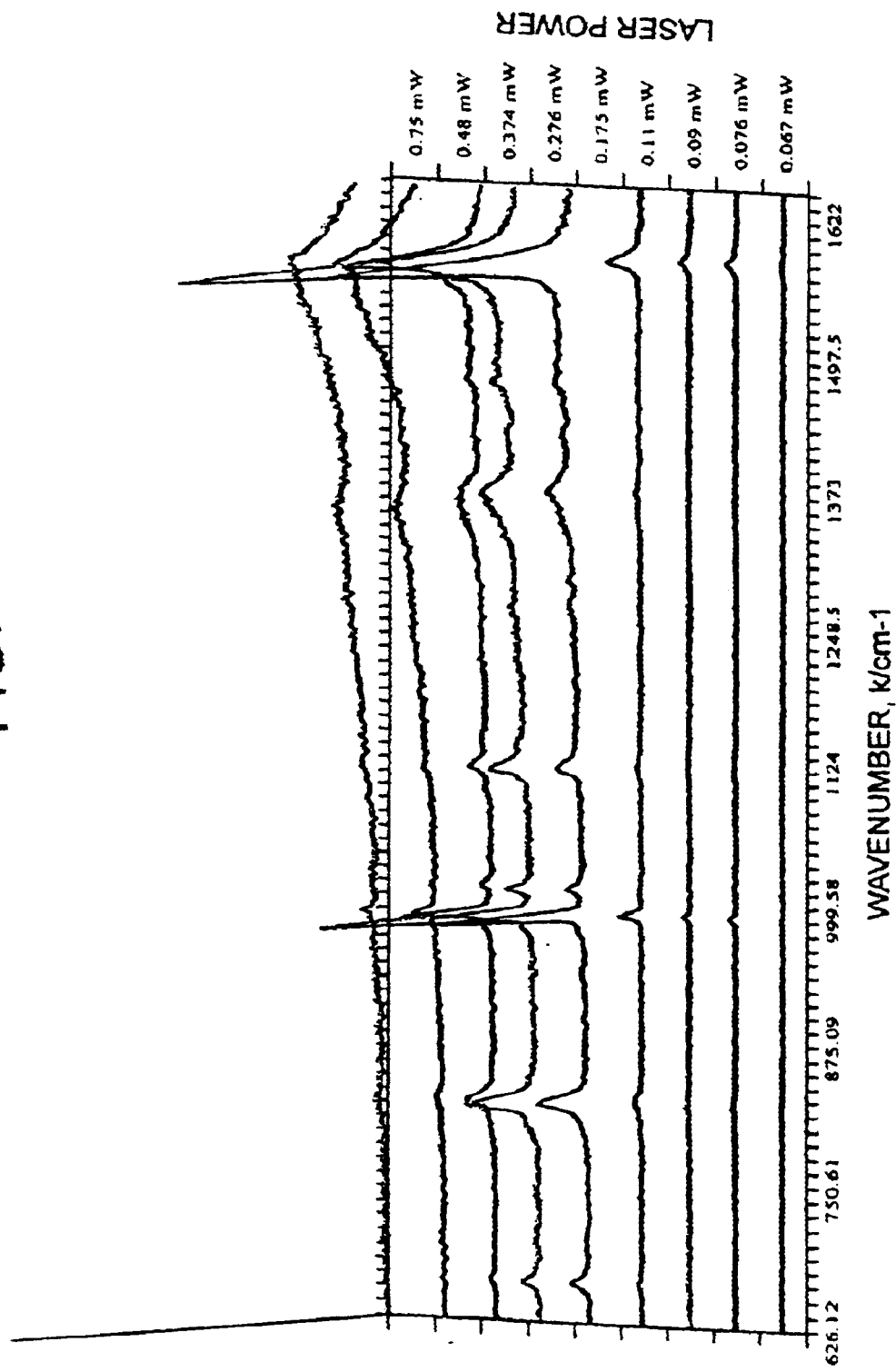
FIG. 4 is a graph showing Raman spectra of the inventive sensor of Example 1 excited at different energy level.

Using the inventive sample of Example 1, Raman spectroscopic analysis was carried out as in Example 1 except that the energy of laser light at the sensor film surface was set at the values shown in FIG. 4. The results are shown in FIG. 4.

It is evident from FIG. 4 that an optimum value exists in the irradiation energy of exciting light. After the Raman spectroscopic analysis, the sensor films were observed under SEM, finding that fine Ag particles of a larger diameter precipitated as the irradiation energy became greater.

BENEFITS OF THE INVENTION

The sensor of the invention is adapted to amplify Raman light by utilizing the localized plasmons generated in proximity to surfaces of fine metal particles in the sensor film. Since a metal compound thin-film is reduced to uniformly precipitate fine metal particles in the thin film according to the invention, a very high amplification factor of Raman light is accomplished. As a consequence, a molecular sensor having a very high sensitivity is available.

What is claimed is:

1. A molecular sensor comprising a sensor film containing a metal compound, wherein when Raman spectroscopic analysis is carried out on the film, the metal compound is reduced and fine particles are generated, and Raman light is amplified by localized plasmons generated by the fine particles.

2. The molecular sensor of claim 1 wherein said sensor film has been formed by physical vapor deposition.

3. The molecular sensor of claim 1 wherein said metal compound is reduced by irradiating electromagnetic wave.

4. The molecular sensor of claim 1 wherein said metal compound is reduced with exciting light used in the Raman spectroscopic analysis.

5. The molecular sensor of claim 1 wherein said metal compound is a metal oxide or metal halide.

6. The molecular sensor of claim 1 wherein said metal compound contains Ag.

7. The molecular sensor of claim 1, wherein said metal compound comprises at least one metal selected from the group consisting of Ag, Au, Cu, Ti and W.

8. The molecular sensor of claim 1, wherein said metal compound comprises at least one metal selected from the group consisting of Ag, Au and Cu.

9. The molecular sensor of claim 1, wherein said metal compound has the formula $AgO_x$, wherein x is in the range of 0.2 to 0.95.

10. The molecular sensor of claim 1, wherein said metal compound has the formula $AgO_x$, wherein x is in the range of 0.3 to 0.7.

11. The molecular sensor of claim 1, wherein said metal compound has the formula $Ag_2O$.

12. The molecular sensor of claim 1, further comprising a substrate in contact with said sensor film, wherein the substrate is a rigid substrate or a flexible resin film.

13. The molecular sensor of claim 1, further comprising a substrate in contact with said sensor film, wherein the substrate is selected from the group consisting of glass, resin, semiconductor, ceramic, and flexible resin film.

14. The molecular sensor of claim 1, wherein said sensor film has a thickness of 1 to 500 nm.

15. The molecular sensor of claim 1, wherein said sensor film has a thickness of 3 to 100 nm.

16. The molecular sensor of claim 1, wherein said fine particles have a mean particle size of 0.1 to 50 nm.

17. The molecular sensor of claim 1, wherein said fine particles have a mean particle size of 0.3 to 20 nm.

18. The molecular sensor of claim 1, wherein an average distance between said fine particles is 0.5 to 50 nm.

19. A Raman spoctroscopic process comprising:
   irradiating a sensor film comprising a metal compound,
   reducing the metal compound to produce fine particles consisting essentially of a metal,
   amplifying the Raman light by localized plasmons generated by the fine particles.

20. The Raman spectroscopic process of claim 19, wherein the fine particles are formed by reduction of a metal compound.

21. The Raman spectroscopic process of claim 19, further comprising detecting at least one compound in a sample, wherein the concentration of said compound in said sample is about $10^{-9}$ mol/liter.

* * * * *